United States Patent [19]
Palcic et al.

[11] Patent Number: 5,507,287
[45] Date of Patent: Apr. 16, 1996

[54] ENDOSCOPIC IMAGING SYSTEM FOR DISEASED TISSUE

[75] Inventors: Branko Palcic; Calum MacAulay; Bruno Jaggi; Stephen Lam, all of Vancouver, Canada; Amedeus E. Profio, Santa Barbara, Calif.; Jaclyn Hung, Vancouver, Canada

[73] Assignee: Xillix Technologies Corporation, Vancouver, Canada

[21] Appl. No.: 428,494

[22] Filed: Apr. 27, 1995

Related U.S. Application Data

[63] Continuation of Ser. No. 82,019, Jun. 23, 1993, abandoned, which is a continuation of Ser. No. 725,283, Jul. 3, 1991, abandoned.

[51] Int. Cl.⁶ ............... A61B 5/00; A61B 1/06; A61B 1/26; G01N 21/64
[52] U.S. Cl. ............ 128/633; 128/634; 128/665; 606/2; 606/15; 606/16; 250/341.1; 250/341.7; 356/318
[58] Field of Search ............ 128/633, 634, 128/664, 665; 606/2, 15, 16; 250/341.1, 341.7, 461.2; 356/318

[56] References Cited

U.S. PATENT DOCUMENTS

| | | | |
|---|---|---|---|
| 4,541,438 | 9/1985 | Parker et al. | 128/654 |
| 4,556,057 | 12/1985 | Hiruma et al. | 128/665 |
| 4,718,417 | 1/1988 | Kittrell et al. | |
| 4,768,513 | 9/1988 | Suzuki | 128/665 |
| 4,773,097 | 9/1988 | Suzaki et al. | 128/665 |
| 4,786,813 | 11/1988 | Svanberg et al. | 250/461.2 |
| 4,821,117 | 4/1989 | Sekiguchi | 128/665 |
| 4,852,579 | 8/1989 | Gilstad et al. | 128/665 |
| 4,930,516 | 6/1990 | Alfano et al. | |
| 4,938,205 | 7/1990 | Nudelman | 606/14 |
| 4,957,114 | 9/1990 | Zeng et al. | 128/665 |
| 5,003,977 | 4/1991 | Suzuki et al. | |
| 5,042,494 | 8/1991 | Alfano | 128/665 |
| 5,071,417 | 12/1991 | Sinofsky | 606/16 |
| 5,078,150 | 1/1992 | Hara et al. | 128/665 |
| 5,091,652 | 2/1992 | Mathies et al. | 250/461.2 |
| 5,115,137 | 5/1992 | Andersson-Engels et al. | 250/461.2 |
| 5,131,398 | 7/1992 | Alfano et al. | 128/665 |

FOREIGN PATENT DOCUMENTS

| | | |
|---|---|---|
| 0215772 | 3/1987 | European Pat. Off. |
| 2203831 | 10/1988 | United Kingdom |
| 86/02730 | 5/1986 | WIPO |
| 90/10219 | 9/1990 | WIPO |
| 90/12536 | 11/1990 | WIPO |

OTHER PUBLICATIONS

Alfano et al. (1987) Fluorescence Spectra from Cancerous and Normal Human Breast and Lung Tissues. IEEE Journal of Quantum Electronics. vol. QE–23, No. 10, pp. 1806–1811.

(List continued on next page.)

*Primary Examiner*—Krista M. Zele
*Attorney, Agent, or Firm*—Christensen, O'Connor, Johnson & Kindness

[57] ABSTRACT

Apparatus for imaging diseases in tissue comprising a light source for generating excitation light that includes wavelengths capable of generating characteristic autofluorescence for abnormal and normal tissue. A fibreoptic illuminating light guide is used to illuminate tissue with light that includes at least the excitation light thereby exciting the tissue to emit the characteristic autofluorescence. An imaging bundle collects emitted autofluorescence light from the tissue. The autofluorescence light is filtered into spectral bands in which the autofluorescence intensity for abnormal tissue is substantially different from normal tissue and the autofluorescence intensity for abnormal tissue is substantially similar to normal tissue. An optical system is used to intercept the filtered autofluorescence light to acquire at least two filtered emitted autofluorescence images of the tissue. The acquired images are displayed in real time on a display monitor in such a manner as to delineate abnormal and normal tissue.

18 Claims, 7 Drawing Sheets

OTHER PUBLICATIONS

Anderson–Engels et al. (1989) Tissue Diagnostics Using Laser–Induced Fluorescence. Ber. Bunsenges. Phys. Chem. 93; pp. 335–342.

Coffey et al. (1984) Evaluation of Visual Acuity During Laser Photoradiation Therapy of Cancer. Lasers in Surgery and Medicine 4, pp. 65–71.

Cothren et al.; Gastrointestinal Tissue Diagnosis by Laser––Induced Fluorescence Spectroscopy at Endoscopy Gastrointestinal Endoscopy vol. 36, No. 2, pp. 105–111.

Dougherty et al. (1990) Cutaneous Phototoxic Occurences in Patients Receiving Photofrin. Lasers in Surgery and Medicine 10, pp. 485–488.

Hirano et al. (1989) Photodynamic Cancer Diagnosis and Treatment Systems Consist Consisting of Pulse Lasers and an Endoscopic Spectro–Image Analyzer. Lasers in Life Sciences 3(1); pp. 1–18.

Hung et al. (1991) Autofluorescence of Normal and Malignant Bronchial Tissue; Lasers in Surgery and Medicine 11, pp. 99–105.

Ikeda (1988) New Brochial TV Endoscopy System. Elsevier Science Publishers B. V. Biomedial Press.

Kapadia et al. (1990) Laser–Induced Fluorescence Spectroscopy of Human Colonic Mucosa; Gastroenterology 99, pp. 150–157.

Kato et al. (1985) Early Detection of Lung Cancer by Means of Hematoporphyrin Derivative Fluorescence and Laser Photoradiation. Clinics in Chest Medicine vol. 6, No. 2, pp. 237–253.

Kato et al. (1990) Photodynamic Diagnosis in Respiratory Tract Malignancy Using an Excimer Dye Laser System, J. of Photochemistry and Photobiology, B:Biology, 6, pp. 189–196.

Lam et al. Fluorescence Detection. Advances in the Diagnosis and Therapy of Lung Cancer.

Lam et al. (1990) Detection of Lung Cancer by Ratio Fluorometry with and without Photofrin II; SPIE Proc. 1201, pp. 561–568.

Lam et al. (1990) Fluorescence Imaging of Early Lung Cancer. IEEE Eng. Med. Biol. 12 Ann. Int. Conf.

Lam et al. (1990) Detection of Early Lung Cancer Using Low Dose Photofrin II; Chest, vol. 97, pp. 333–337.

Lam et al. (1991) Mechanism of Detection of Early Lung Cancer by Ratio Fluorometry; Lasers in Life Sciences, 4(2); pp. 67–73.

Mullooly et al. (1990) Dihematoporphyrin Ether–Induced Photosensitivity in Photosensitivity in Laryngeal Papilloma Patients. Lasers in Surgery and Medicine 10; pp. 349–356.

Palcic et al. (1990) Development of a Lung Imaging Fluorescence Endoscope. Proceedings of the 12th Annual Intl. Conference of the IEEE Engineering in Medicine and Biology Society. vol. 12, No. 1.

Palcic et al. (1990) The Importance of Image Quality for Computing Texture Features in Biomedical Specimens. SPIE Proc. 1205, pp. 155–162.

Palcic et al. (1991) Lung Imaging fluorescence Endoscope: A Device for Detection of Occult Lung Cancer. Medical Design and Material.

Palcic et al. (1991) Lung Imaging Fluorescence Endoscope: Development and Experimental Prototype, SPIE vol. 1448; pp. 113–117.

Palcic et al. (1991) Detection and Localization of Early Lung Cancer by Imaging Techniques Chest. vol. 99, pp. 742–743.

Peak, et al. (1986) DNA–to–Protein Crosslinks and Backbone Breaks Caused by FAR– and NEAR–Ultraviolet and Visible Light Radiations in Mammalian Cells. Mechanisms of DNA Damage and Repair, Implications for Carcinogenisis and Risk Assessment, pp. 193–202.

Profio et al. (1986) Digital Background Subtraction for Fluorescence Imaging; Med. Phys. 13(5); pp. 717–727.

Profio et al. (1991) Endoscopic Fluorescence Detection of Early Lung Cancer. SPIE vol. 1426, pp. 44–46.

Rava et al. (1991) Early Detection of Dysplasia in Colon and Bladder Tissue Using Laser Induced Fluorescence. SPIE vol. 1426; pp. 68–78.

Razum et al. (1987) Skin Photosensitivity: Duration and Intensity Following Intravenous Hematoporphyrin Derivatives, HpD and DHE, Photochemistry and Photobiology vol. 46, No. 5; pp. 925–928.

Richards–Kortum et al. (1991) Spectroscopic Analysis Biochemistry and Photobiology, vol. 53, No. 6, pp. 777–786.

Tang et al. (1989) Spectroscopic Differences Between Human Cancer and Normal Lung and Breast Tissues. Lasers in Surgery and Medicine 9; pp. 290–295.

Wagnieres et al. (1990) Photodetection of Early Cancer by Laser Induced Fluorescence of a Tumor–Selective Dye: Apparatus Design and Realization. SPIE Proc. 1203; pp. 43–52.

Wooten et al. (1988) Prospective Study of Cutaneous Phototoxicity After Systemic Hematoporphyrin Derivative Lasers in Surgery and Medicine 8, pp. 294–300.

Andersson–Engels et al. (1991) Fluorescence Characteristics of Atherosclerotic Plaque and Malignant Tumors; SPIE. vol. 1426. pp. 31–43.

Profio et al. (1979) Laser Fluorescence Bronchosoope for Localization of Occult Lung Tumors; Med Phys 6(6) pp. 523–525.

Profio et al. (1984) Fluorometer for Endoscopic Diagnosis of Tumors Med Phys 11(4); pp. 516–520.

Hayata et al. (1982) Fiberoptic Bronchoscopic Laser Photoradiation for Tumor Localization in Lung Cancer; Chest 82, pp. 10–14.

Montan et al; Multicolor Imaging and Contrast Enhancement in Cancer–Tumor Localization Using Laser–Induced Fluorescence in Hematoporphyrin–derivative–bearing Tissue; Opt Letters 10(2) (1985) pp. 56–58.

Pollack et al.; B Vitamins in Cancerous Tissues; Cancer Res 2(11) (1942) pp. 739–743.

Excitation: 405nm

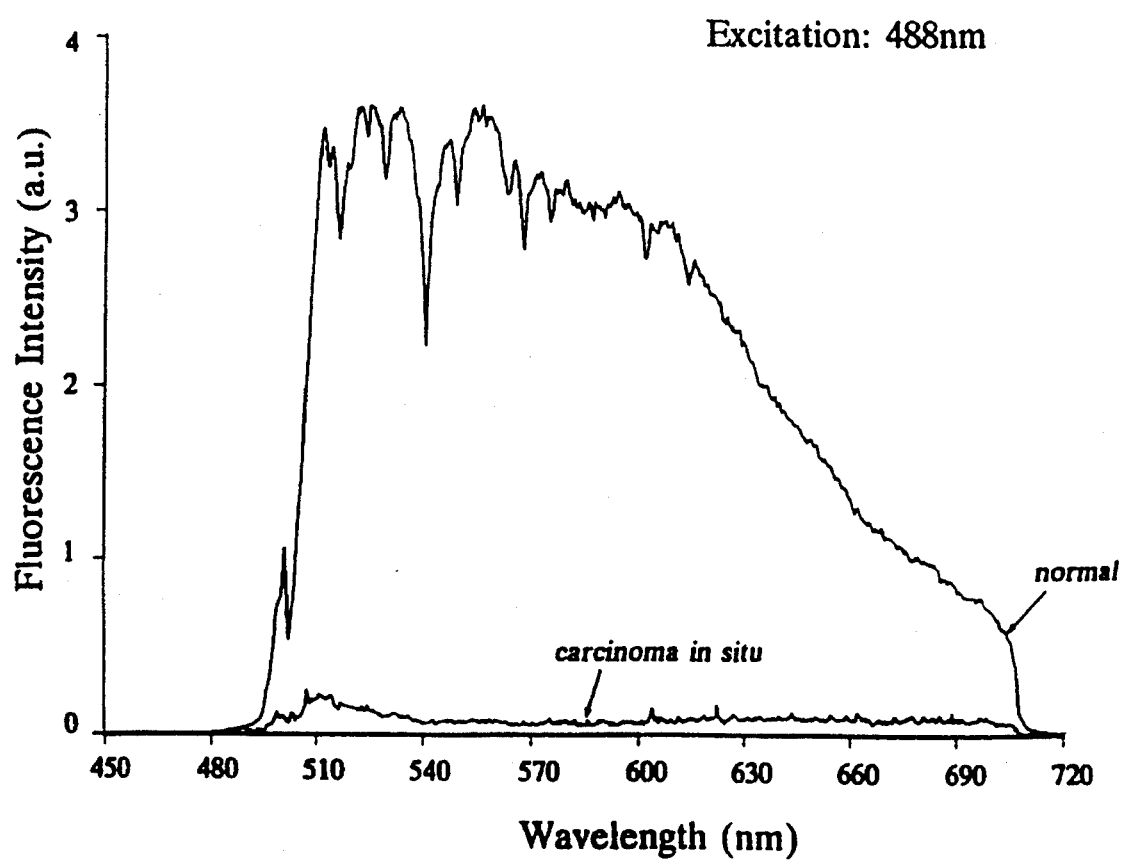

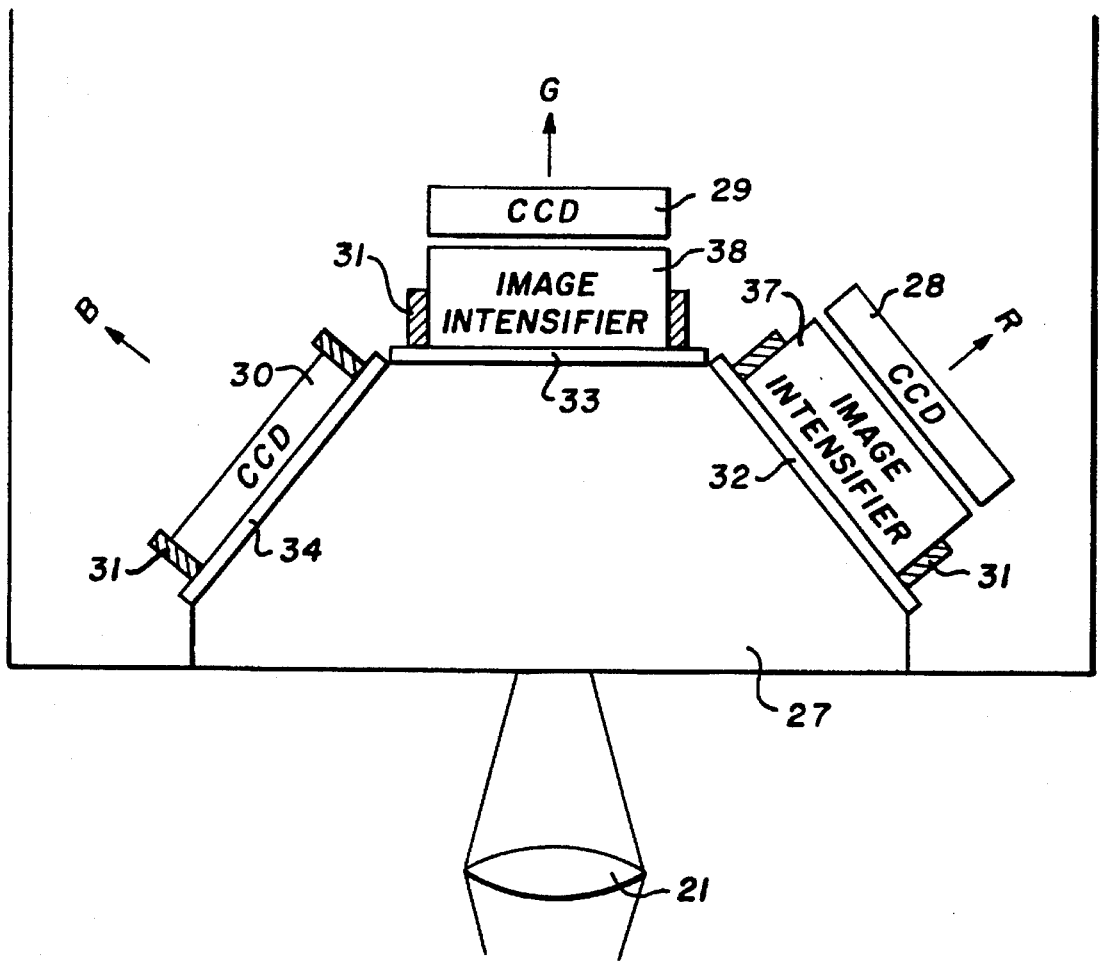

ENDOSCOPIC IMAGING SYSTEM FOR DISEASED TISSUE

This application is a continuation application based on prior application Ser. No. 08/082,019, filed on Jun. 23, 1993, now abandoned, which was a continuation of Ser. No. 07/725,283 filed Jul. 3, 1991 now abandoned.

FIELD OF THE INVENTION

This invention relates to an apparatus for imaging abnormal tissues in the body to locate and identify areas that are otherwise not recognizable by white light endoscopy. The invention is particularly suited for imaging abnormal bronchial tissues to detect conditions such as inflammation, denudation, dysplasia and non-invasive early cancer (carcinoma in situ).

BACKGROUND OF THE INVENTION

At present, the most effective method for examination of body cavities in human patients is by endoscopes. For examination of the air passages of the lung, a flexible endoscope is usually used, commonly referred to as a bronchoscope. Bronchoscopes, like all endoscopes, employ visible white light to illuminate the surface under examination. The illuminating light is brought into the air passages (bronchi) of the lungs via a fiberoptic illuminating light guide. The reflected and scattered light from the bronchial tissues is captured by a projection lens which focuses the image into the bronchoscope's imaging bundle. The imaging bundle is composed of several thousand individually wrapped fibers, which transmit a coherent image to the exterior of the body. This image is then projected through the ocular of the bronchoscope for human observation. A colour video camera can be attached to the eyepiece of the bronchoscope such that colour images of scattered/reflected white (broadband) light can be viewed on a colour video monitor.

Using a conventional bronchoscope, large invasive cancers can be readily seen. However, focal inflammation, denudation, dysplasia, and early lung cancers cannot be readily seen by such an apparatus.

Several methods have been developed to visualize small early lung cancers which are difficult to detect by ordinary white light bronchoscopy. All of these involve the use of tumour localizing drugs, e.g. Haematoporphyrin derivatives or Porfimer sodium, which have been shown to be preferentially retained in tumour tissues. Some of these drugs also fluoresce and their fluorescence can be detected by non-imaging and imaging devices (Profio AE et al., Med Phys 6:532–535, 1979; Prorio AE et al., Med Phys 11:516–520, 1984; Profio AE et al., Med Phys 13:717–721, 1986; Hayata Y et al., Chest 82:10–14, 1982; Kato A, Cortese DA, Clin Chest Med 6:237–253, 1985; Montan S et al., Opt Letters 10:56–58, 1985). The drawback of these techniques is the use of drugs which may have serious side effects and therefore may not be appropriate for diagnostic purposes. In addition, the use of non-imaging devices such as the ratio fluorometer probe (Profio et al., Med. Phys 11:516–520, 1984) cannot delineate the exact site and dimensions of the abnormal areas.

An alternative approach for detecting invasive tumours has been proposed by Alfano et al in U.S. Pat. No. 4,930,516 issued Jun. 5, 1990. Alfano discloses a method of detecting cancers on the basis that the fluorescence spectra of cancerous tissues is different from normal tissues in that the maximal fluorescence peak of tumour tissues is blue shifted to lower wavelengths (from 531 nm to 521 nm). These observations were made based on in vitro measurements in excised, large (invasive) animal and human tumours but have not been reported on human tumours in vivo. In addition, there are no reports of other abnormal tissues such as inflamed or pre-cancerous tissues. We have measured tissue autofluorescence in human patients in vivo using different excitation wavelengths including 405 nm, 442 nm, and 488 nm by a specially designed optical multichannel analyzer which can be attached to a conventional bronchoscope. Contrary to the observation by Alfano et al., we did not find any difference in the shape of the fluorescence spectrum between normal and tumour tissues using these excitation wavelengths. In particular, there was no blue shift of the emission peaks. We observed a significant difference in the overall fluorescence intensity especially in the green region of the visible spectrum. A significant but a lesser decrease in the overall fluorescence intensity was also found in precancerous and non-cancerous lesions (dysplasia and metaplasia).

The decreased green fluorescence may be attributed to a reduced level of oxidized form of riboflavin. Riboflavin emits strongly in the green region and is believed to be predominantly responsible for the strong green fluorescence in normal human lung tissue. In the cancerous tissues, much less riboflavin was found (Pollack MA et al., Cancer Res 2:739–743, 1942) and/or is present in the reduced state. This may account for the reduced autofluorescence in premalignant and malignant bronchial tissues.

Tests were conducted revealing examples of such decreased tissue autofluorescence for dysplastic bronchial tissue, and carcinoma in situ. It was determined that the main difference between abnormal and normal tissues is manifested by a greatly reduced fluorescence intensity in the region of the spectrum from 480 nm–600 nm. At wavelengths greater than approximately 635 nm, the tissue autofluorescence is approximately the same between abnormal and normal tissues. Test were conducted using excitation light of 442 nm, 405 nm and 488 nm and abnormal tissue results were compared to normal tissue results. All of these data were obtained in vivo during standard fiberoptic bronchoscopy using the optical multichannel analyzer.

Because of the observed large decrease in the emitted fluorescence without a change in the spectral profile in the abnormal tissues, methods using ratioing of two or more wavelengths that was originally described by Profio and coworkers and then studied in patients who have received fluorescent drugs such as Photofrin (Profio et al., Med. Phys. 11:516–520, 1984) generally will not differentiate abnormal from normal bronchial tissues using autofluorescence alone.

We have invented and constructed an apparatus which exploits differences in autofluorescence intensity for the detection and delineation of the extent of abnormal areas in the human body, particularly the lung.

SUMMARY OF THE INVENTION

The present invention provides an imaging apparatus that uses autofluorescence characteristics of tissues to detect and delineate the extent of abnormal tissues in human patients in vivo. Capture and analysis of the autofluorescence images is achieved using a highly sensitive detector such as an image intensified CCD camera. A pseudo image is generated by sending one image to the red channel and one image to the green channel of an RGB video monitor. By capturing the two images simultaneously or sequentially within a few milliseconds, pseudo image generation in real time can be achieved. The pseudo images can clearly delineate the diseased tissue from the surrounding normal tissue.

Accordingly, the present invention provides an apparatus for imaging diseases in tissue comprising:

a light source for generating excitation light that includes wavelengths capable of generating characteristic autofluorescence for abnormal and normal tissues;

means for illuminating tissue with light that includes at least said excitation light thereby exciting the tissue to emit said characteristic autofluorescence;

collecting means for gathering emitted autofluorescence light from said tissue;

means for filtering said autofluorescence light into spectral bands in which said autofluorescence intensity for abnormal tissue is substantially different from normal tissue and said autofluorescence intensity for abnormal tissue is substantially similar to normal tissue;

optical means for intercepting said filtered autofluorescence light to acquire at least two filtered emitted autofluorescence images of the tissue; and display means for displaying said acquired images in such a manner as to delineate abnormal and normal tissue.

In a preferred embodiment, the apparatus of the present invention is used with a standard bronchoscope for imaging abnormal bronchial tissues.

BRIEF DESCRIPTION OF THE DRAWINGS

Aspects of the present invention are illustrated, merely by way of example, in the accompanying drawings in which:

FIGS. 1a to 1d provide examples of autofluorescence spectrums at selected excitation wavelengths which indicate the difference between abnormal and normal tissue;

FIG. 4c shows a still further filtering and optical means in which a prism element is incorporated to allow two fluorescence images to be acquired simultaneously together with a reflected/scattered excitation light image.

DESCRIPTION OF THE PREFERRED EMBODIMENTS

Figure 1A:
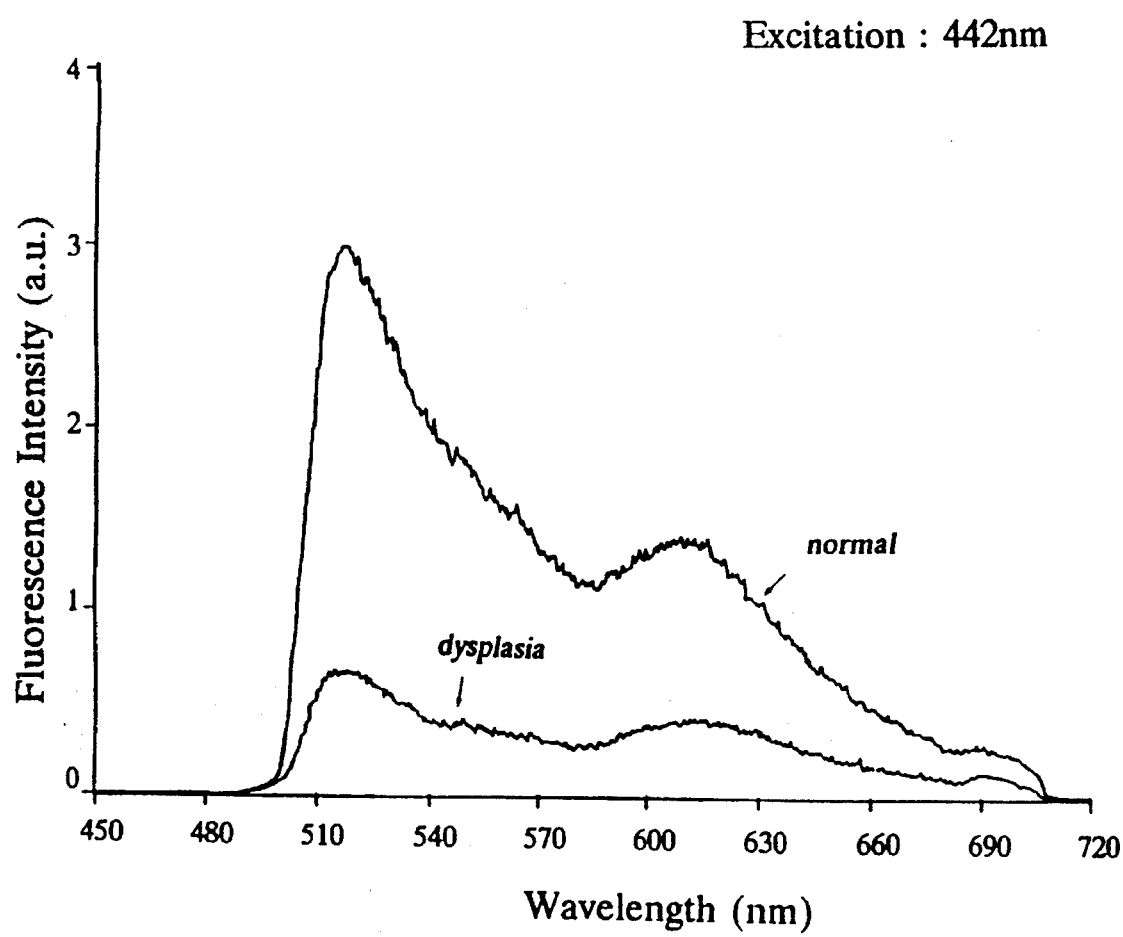
Figure 1B:
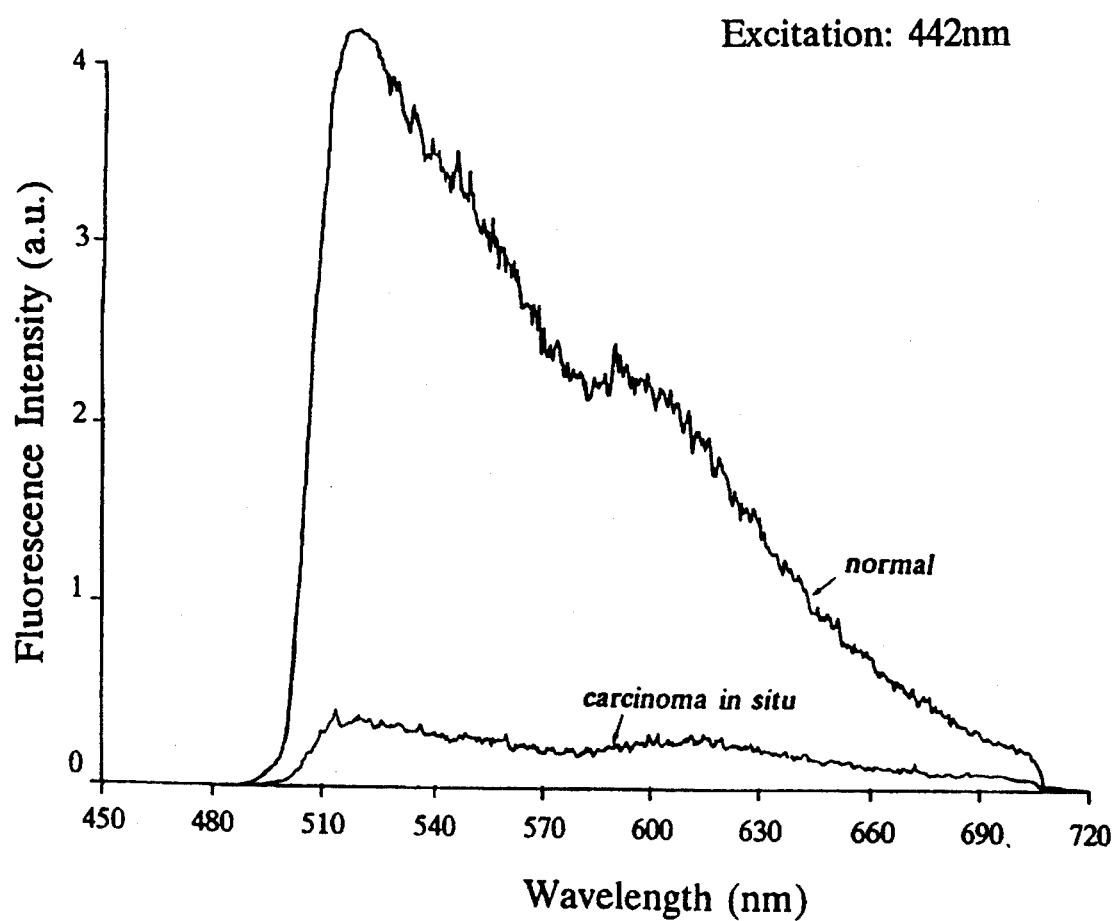
Figure 1C:
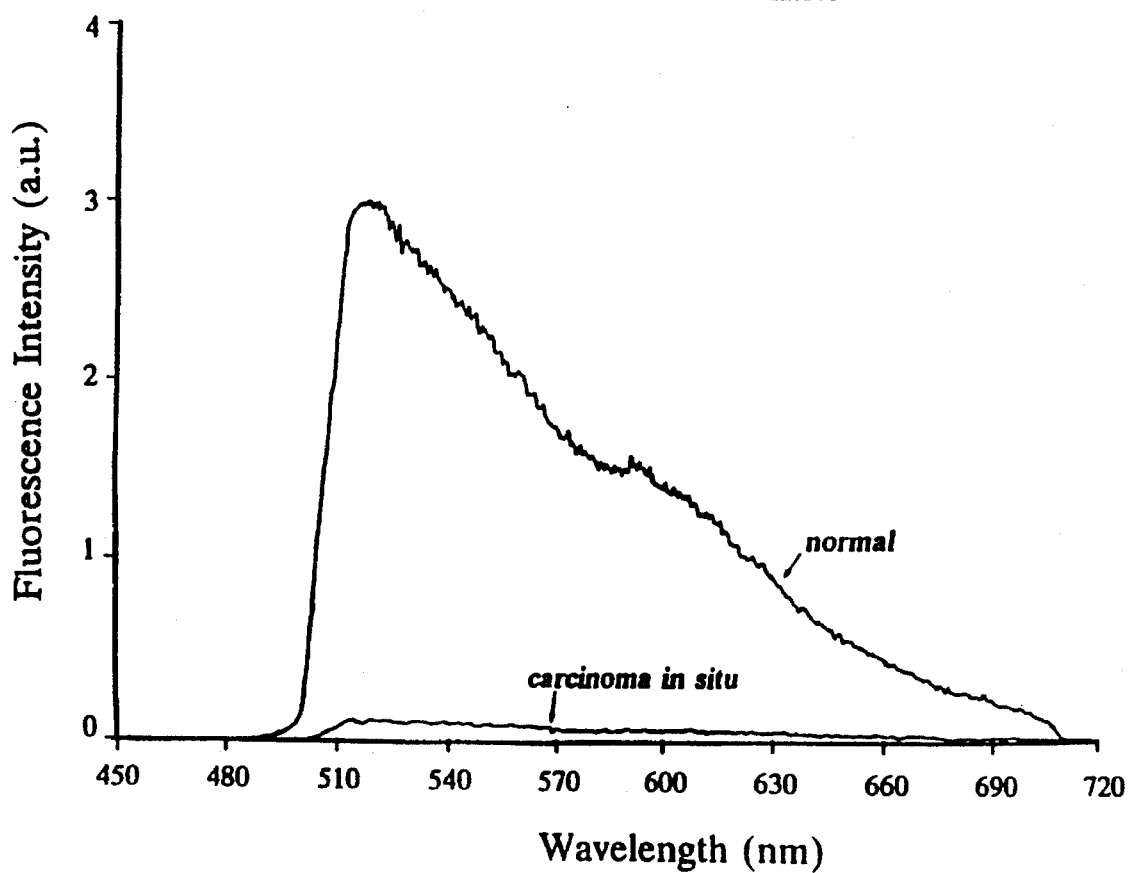

FIG. 1 shows examples of decreased tissue autofluorescence for dysplastic bronchial tissue and carcinoma in situ. The main difference between abnormal and normal tissues is manifested by a greatly reduced fluorescence intensity in the region of the spectrum from 480 nm–600 nm. At wavelengths greater than approximately 635 nm, the tissue autofluorescence is approximately the same between abnormal and normal tissues. For the results in FIG. 1a and 1b, a 442 nm Helium Cadmium laser light was used to excite the tissues. FIG. 1a shows tissue autofluorescence spectra of normal and dysplastic tissues and FIG. 1b shows a carcinoma in situ (CIS) lesion compared to the normal tissue of a different patient. Similar results were found when employing other excitation light, e.g. 405 nm, FIG. 1c and 488 nm, FIG. 1d. In both cases carcinoma in situ patients are compared to their normal lung tissue. All of these data were obtained in vivo during standard fiberoptic bronchoscopy using an optical multichannel analyzer.

The apparatus of the present invention is designed to exploit the difference in fluorescence intensity in different regions of the spectrum to identify and delineate abnormal tissue.

Figure 2:
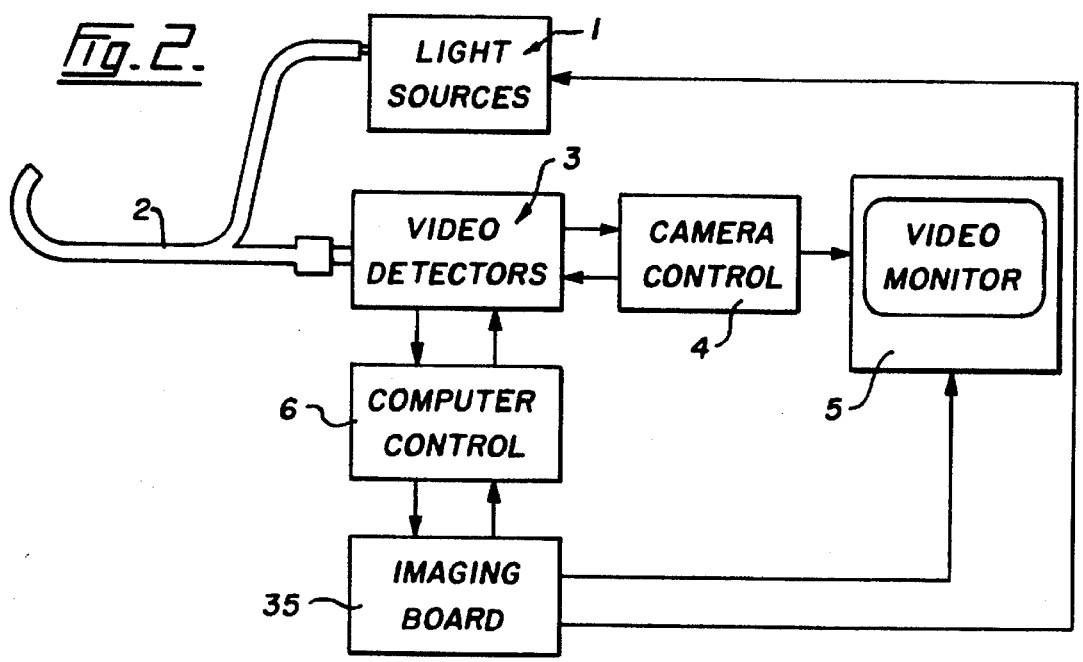
FIG. 2 is a schematic diagram showing the apparatus of the present invention useful for imaging abnormal lung tissue.

The apparatus of the present invention adapted for use in examining bronchial tissues of the lung in patients is schematically illustrated in FIG. 2. As such, the apparatus is integrated with a conventional bronchoscope used for examining bronchial tissue of the lung.

Figure 3:
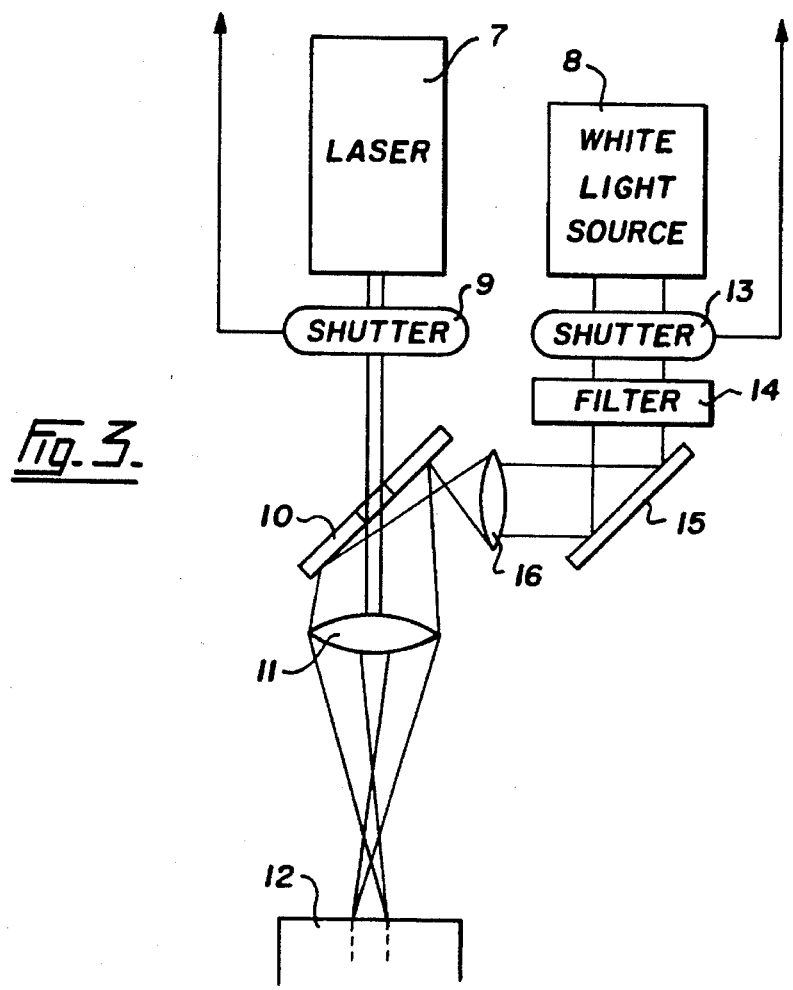
FIG. 3 shows details of the illumination module.

There is a light source 1 for generating excitation light that includes wavelengths capable of generating characteristic autofluorescence spectra for abnormal and normal tissue. The light source 1 is shown in greater detail in FIG. 3 and preferably includes a laser light source 7 capable of producing excitation light at a selected desirable wavelength. A white light source such as an incandescent Xenon light source 8 can be used for white light illumination when desired. The laser light source 7 is use to generate pseudo images derived from tissue autofluorescence while the white light source is used to generate colour images of reflected/scattered white light.

The light from each light source passes through synchronizing means that allow for alternate illumination of the tissue by the laser light and the white light source. In the embodiment illustrated in FIG. 3, the synchronizing means comprises blocking means in the form of electronically controlled shutters 9 and 13 associated with laser light source 7 and Xenon light source 8, respectively. When shutter 9 is open to allow laser light to pass, shutter 13 is closed to prevent passage of white light and vice versa. The light from the laser light source 7 passes through shutter 9 when open, a mirror with a pin hole 10, and a lens 11 which focuses the laser light onto means for illuminating the tissue with light comprising a conventional bronchoscope light guide 12. Light guide 12 conducts the excitation light to the tissue area under examination. The tissue, upon illumination with the laser light, emits its characteristic autofluorescence for abnormal and normal tissue. To generate regular white light illumination images, shutter 9 is closed and previously closed shutter 13 is opened to allow the light from Xenon light source 8 to pass through shutter 13. The white light is then filtered by a neutral density filter set 14, reflected by a mirror 15, and passes through a lens 16 which focuses the light onto bronchoscope light guide 12 after being reflected off mirror 10 and through lens 11. The neutral density filter set 14 is used to condition the light from the Xenon source such that it is of the appropriate intensity for the light sensors used in the apparatus. Thus the white light conducted to the tissue illuminates the tissue under examination. Light guide 12 ensures that the light is evenly dispersed over the area under examination.

In the present embodiment, the bronchoscope provides the collecting means to gather images in the form of the bronchoscope lens (not shown) which collects scattered and reflected light, or emitted autofluorescence light from within the lung for transmission out of the body by imaging bundle 2 of the bronchoscope. This collected light is transmitted to a focusing lens 21 of the bronchoscope ocular coupled to the imaging bundle.

From the ocular of the bronchoscope, the collected light enters the image acquisition module 3 which includes means for filtering the autofluorescence light and optical means for intercepting the filtered light. Various embodiments of image acquisition module 3 are possible.

Figure 4A:
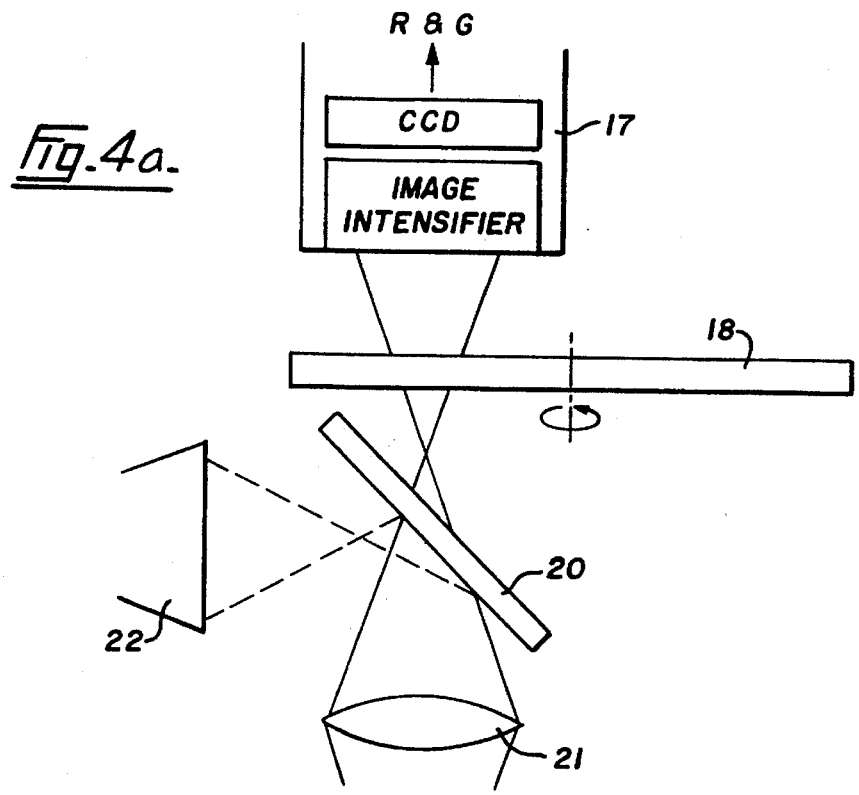
FIG. 4a shows the filtering and optical means of the present invention in which a single sensitive detector is used to acquire fluorescence images sequentially.

FIG. 4a illustrates an image acquisition module that includes filtering means and optical means that allow for acquisition of emitted autofluorescence images sequentially. In this embodiment, the means for filtering the autofluorescence light comprises a series of filters that are sequentially insertable into the path of the emitted autofluorescence light to generate a sequence of filtered autofluorescence images. Filter wheel 18 is provided and is rotatably mounted beneath the optical means of the image acquisition module. When laser excitation light 7 is used, it is necessary to filter the autofluorescence light generated into at least two spectral bands. In one spectral band, the autofluorescence intensity for abnormal tissue is substantially different from that of normal tissue and in the other spectral band, the autofluorescence intensity is substantially similar to that of normal tissue. For example, in accordance with the characteristic spectral bands indicated in FIGS. 1a to 1d for lung examination, filter wheel 18 would be fitted with two filters. For laser excitation light of 442 nm or 405 nm, a green filter of 500+ −20 nm and a red 630 nm longpass filter would be used. The green filter would filter the autofluorescence light into a spectral band in which the autofluorescence intensity for abnormal tissue is substantially different from that of normal tissue while the red longpass filter would filter the light into a spectral band in which the autofluorescence intensity is substantially similar for abnormal and normal tissue. The two filters are mounted in filter wheel 18 such that each covers one half of the filter surface. By rotating filter wheel 18 at an appropriate speed, red and green filtered autofluorescence images can be captured sequentially by optical means in the form of a single highly sensitive detector 17 such as an image intensified CCD camera.

The foregoing image acquisition module also includes additional optical means for capturing reflected/scattered white light images when white light source 8 is providing illumination of the tissue. A movable mirror 20 is provided that is insertable into the path of the collected light transmitted by ocular lens 21. Mirror 20 is positionable to deflect white light into a colour video camera 22 for acquisition of white light images. Necessarily, the movement of mirror 20 is controlled such that the mirror deflects the collected light into video camera 22 only when white light source 8 is providing illumination. Using white light source 8, colour images can be generated on a colour monitor in the same way as in conventional bronchoscopy. When laser light source 7 is illuminating the tissue, mirror 20 is removed from the light pass to allow for filtering of the autofluorescence light and subsequent acquisition by detector 17.

Figure 4B:
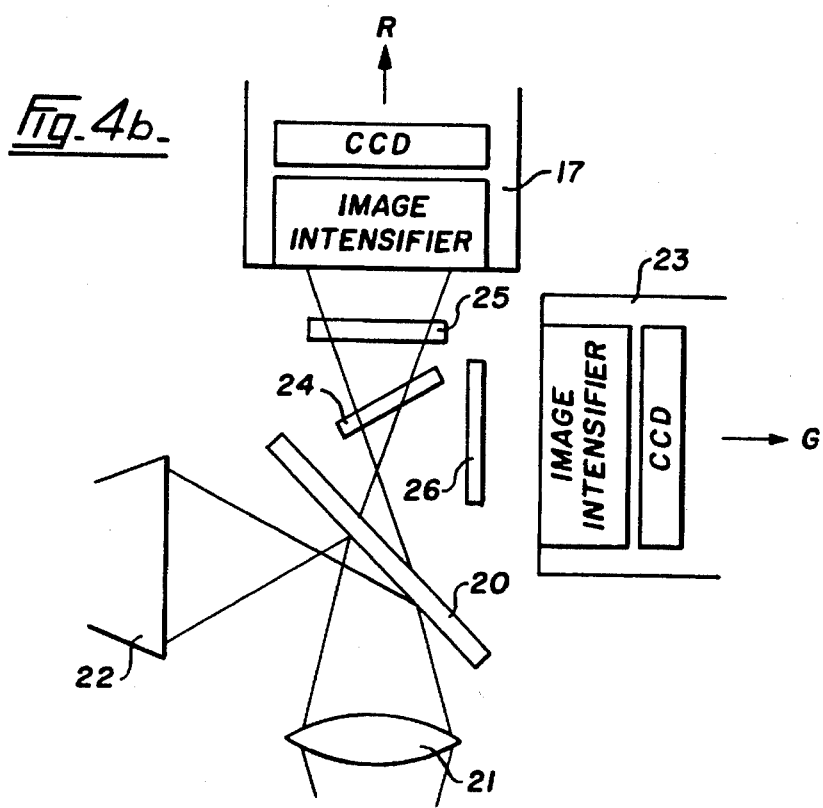
FIG. 4b shows alternative filtering and optical means in which fluorescence images are acquired simultaneously using two sensitive cameras.

FIG. 4b illustrates an alternative arrangement of image acquisition module 3 in which the optical means comprises at least two photodetectors that acquire filtered autofluorescence images simultaneously. Each photodetector has associated filtering means. For simultaneous collection of autofluorescence images, filter wheel 18 of the embodiment of FIG. 4a is replaced by beam splitting means in the form of a dichroic mirror 24 which allows the red light >600 nm to pass but reflects the shorter wavelengths. In this case, additional filters 25 and 26 for exact selection of the desired autofluorescence light can be employed and the respective images are focused onto two independent sensitive photodetectors such as image intensified CCD cameras 17 and 23. In FIG. 4, filter 25 is a red 630 nm longpass filter to further filter red light passed by dichroic mirror into a spectral band in which autofluorescence intensity is substantially similar for normal and abnormal tissue. Filter 26 is a green filter of 500+−20 nm for filtering the autofluorescence light into a spectral band in which the autofluorescence intensity for abnormal tissue is substantially different from that of normal tissue. Images acquired by the image intensified CCD camera 17 and/or image intensified CCD camera 23 are fed into red and green input channels of an RGB colour monitor 5 (FIG. 1).

As in the arrangement of FIG. 4a, reflected/scattered white light images created by white light source 8 are captured by a colour camera 22 and are displayed directly onto the colour monitor for visualization of the examined site using an identical movable mirror 20 insertable into the light path whenever white light source 8 is providing illumination.

FIG. 4c illustrates a further embodiment of an image acquisition module for use with the apparatus of the present invention. A prism element 27 is provided that simultaneously splits collected light into a plurality of directions. By alternating between laser light source 7 and white light source 8, it is possible to capture sequentially both autofluorescence images and white light images within a 33 millisecond cycle time, therefore allowing a view of white (broadband) light colour images and pseudo fluorescence images at the same time on display means.

A specially developed camera with three photodetectors 28, 29 and 30 is provided. The prism 27 splits the collected light into three images which are then captured by the three separate detectors. Photodetectors 28 and 29 comprise CCD imaging devices that are provided with associated image intensifiers 37 and 38 and photodetector 30 is a regular CCD imaging device. Each photodetector has its own filter 32, 33 and 34, respectively, as well as an x,y,z micropositioner 31. Filters 32 and 33 are the same as in the previous embodiments: a 500+ −20 nm green filter 33, and a 630 nm long pass filter 33. CCD imaging device 30 has an associated broadband blue filter 34.

As best shown in FIG. 2, associated camera control electronics 4 are such that they generate three image signals, a red signal produced by red filter 32 and intensified CCD imaging device 28, a green signal produced by green filter 33 and intensified CCD imaging device 29, and a blue signal produced by blue filter 34 and non-intensified CCD imaging device 30.

In all of the above embodiments, one can employ a specially designed CCD imaging device instead of an image intensified detector. For example, particularly when a lesser spatial resolution is required, several pixels of a sensitive scientific CCD detector can be electronically combined into a single very large pixel which allows very low signals to be detected.

All or some of the image signals produced by the various image acquisition modules of the present invention may be displayed directly on colour monitor 5 or processed by image processing means prior to display. The apparatus of the present invention can switch between white (broadband) light illumination and laser illumination in one thirtieth of a second.

Under laser illumination, the image acquisition module of FIG. 4c can collect autofluorescence images of the tissue over two selected areas of the spectra and a blue scattered/reflected excitation light image all simultaneously. These images can be combined either visually or mathematically via image processing means to make distinguishable the various tissue types present in the image. With white light illumination, the apparatus can collect red, green and blue reflected/scattered light images so as to make possible a regular colour image of the tissues.

Furthermore, the colour image can be combined with the autofluorescence blue laser illuminated images to enhance the detection, localization, and delineation of the various tissues.

For different tissues and/or diseases, a different combination of filters is employed to enhance the differences between normal and diseased tissues based on the characteristic emitted autofluorescence light of the diseased tissue under study.

As shown in FIG. 2, the present invention is preferably provided with image processing means in the form of an imaging board 35 associated with a computer 6 that controls and co-ordinates operation of the apparatus. Imaging board 35 allows images to be digitally captured if desired. Board 35 acts to digitize the filtered images provided by the image acquisition modules and enhance the digitized images by application of transformational algorithms to produce pseudo computed images in real time for display on video monitor 5. Alternatively, the digitized images can be stored in computer memory.

The pixel values in the digitized images can be used to calculate a value for each image pixel, using a mathematical transformation, so that all pixels covering the diseased tissue site are clearly different from those of the normal tissue. This process can be used to enhance the images, to enable the measurement of the degree of the disease, and make possible other applications and/or measurements.

Several mathematical algorithms have been developed that allow the creation of different computed pseudo images from the digitized emitted autofluorescence images and scattered/reflected light images, provided the autofluorescence images are captured over the spectral areas that are characteristic and appropriate for the specific tissue disease. Examples of appropriate mathematical algorithms that can be programmed and applied to the digitized images include hue, contrast and intensity functions, principle component decomposition algorithms, logarithm of differences, and subtraction algorithms, all of which delineate normal tissues from the diseased tissues.

One transformation which has been reported with tumour localizing drugs (Profio, Med. Phys. 11:516–520, 1984) was found by us not to be useful for the imaging method; with the exception of large invasive cancers, it often fails to reveal the abnormal areas.

In a preferred embodiment of the present invention, digitization of images and image processing is not required. By employing colour monitor 5 and the human visual system, it is possible to depict differences between the normal and diseased site as differences in perceived colour.

When using the image acquisition module of FIG. 4b having two sensitive CCD cameras, one camera feeds the Red channel and the other feeds the Green channel of the RGB colour monitor 5. The red tissue autofluorescence of the abnormal and normal bronchial tissues is approximately the same. The green tissue autofluorescence is dramatically decreased in the abnormal site compared to normal tissue. Therefore the abnormal site appears much less green and much more reddish and/or sandy colour compared to the surrounding normal tissue which looks bright green as green fluorescence is much more dominant than red fluorescence in normal tissue. This preferred embodiment allows visualization of the diseased sites in real time without any processing of the images and is therefore very inexpensive.

The same result can be achieved using the single CCD camera and filter wheel of the image acquisition module of FIG. 4a. In this case, two sequential red and green fluorescence images must be electronically combined at video rates to be fed as red and green input signals for an RGB monitor.

Alternatively, two different spectral bands of tissue autofluorescence are acquired and interpreted as red and green signals for colour display on a colour monitor. This gives excellent pseudo images of inflamed tissue, dysplastic tissue and non-invasive cancer; clearly delineating these tissues from normal tissue. The decrease in diseased tissue autofluorescence, particularly in the green region, indicates the presence of the disease as well as the severity of the disease.

If tumour localizing drugs are used, the apparatus of the present invention can be used to visualize small and large tumours. For example, for drugs such as Photofrin (Porfimer sodium), the same filters can be used as the drug emits fluorescence at peak values of 630 nm and 690 nm. In this case all sites where the drug has localized will also be clearly delineated from the normal tissues.

Although the present invention has been described in some detail by way of example for purposes of clarity and understanding, it will be apparent that certain changes and modifications may be practised within the scope of the appended claims.

We claim:

1. Apparatus for imaging diseases in tissue using autofluorescence comprising:

a visible light source for generating excitation light that includes wavelengths that generate characteristic autofluorescence for abnormal and normal tissue;

means for illuminating tissue with light from the visible light source that includes at least said excitation light thereby exciting tissue to emit said characteristic autofluorescence;

collecting means for gathering a reflected excitation light and an emitted autofluorescence light from said tissue;

a dichroic mirror positioned to receive the reflected excitation light and the emitted autofluorescence light gathered by the collecting means, the dichroic mirror operating to separate the spectral components of said autofluorescence light into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from light within the first spectral band;

a second optical filter positioned to receive the light within the second spectral band;

a first detector array for receiving the autofluorescence light within the first spectral band and for producing a first auto fluorescence image of the tissue;

a second detector array for receiving the autofluorescence light within the second spectral band and for producing a second autofluorescence image of the tissue; and a color monitor having at least a first and second color input whereby the first color input is coupled to receive the first autofluorescence image and the second color input is coupled to receive the second autofluorescence image to create a combined, display image in which said abnormal and normal tissue are displayed on the color monitor.

2. The apparatus of claim 1, in which the visible light source is a laser.

3. The apparatus of claim 1, in which the visible light source is a xenon light source.

4. The apparatus of claim 1, wherein the dichroic mirror has a cutoff wavelength of 600 nanometers.

5. The apparatus of claim 1, wherein the first optical filter is a band pass filter having a center frequency of about 500 nanometers and a band-pass of about +/−20 nanometers.

6. The apparatus of claim 1, wherein the second filter is a red, long pass filter having a cutoff frequency of 630 nanometers.

7. The apparatus of claim 1, in which the means for illuminating tissue is a fiber optic light guide.

8. The apparatus of claim 7, in which the collecting means is an imaging bundle and a focusing lens disposed within the fiber optic light guide.

9. The apparatus of claim 1, wherein the first color input is a green color input and the second color input is a red color input.

10. Apparatus for imaging diseases in tissue using autofluorescence comprising:

a visible light source for generating excitation light that includes wavelengths that generate characteristic autofluorescence for abnormal and normal tissue;

means for illuminating tissue with light from the visible light source that includes at least said excitation light thereby exciting tissue to emit said characteristic autofluorescence;

collecting means for gathering a reflected excitation light and an emitted autofluorescence light from said tissue;

means for separating the spectral components of the collected reflected excitation light and the emitted autofluorescence light gathered by the collecting means, into at least a first spectral band including the reflected excitation light and the emitted autofluorescence light having wavelengths where an autofluorescence intensity for abnormal tissue is substantially different from normal tissue and a second spectral band different from said first spectral band including the emitted autofluorescence light having wavelengths where an autofluorescence intensity for abnormal tissue is substantially similar to normal tissue;

a first optical filter positioned to receive the light within the first spectral band, said first filter operating to remove the reflected excitation light from light within the first spectral band;

a second optical filter positioned to receive the light within the second spectral band;

a first detector array for receiving the autofluorescence light within the first spectral band and for producing a first autofluorescence image of the tissue;

a second detector array for receiving the autofluorescence light within the second spectral band and for producing a second autofluorescence image of the tissue; and a color monitor having at least a first and second color input whereby the first color input is coupled to receive the first autofluorescence image and the second color input is coupled to receive the second autofluorescence image to create a combined, display image in which said abnormal and normal tissue are displayed on the color monitor.

11. The apparatus of claim 10, wherein the means for separating the spectral components of the collected reflected excitation light and the autofluorescence light into the first and second spectral bands comprises a prism.

12. The apparatus of claim 10, in which the visible light source is a laser.

13. The apparatus of claim 10, in which the visible light source is a xenon light source.

14. The apparatus of claim 10, wherein the first optical filter is a band pass filter having a center frequency of about 500 nanometers and a band-pass of about +/−20 nanometers.

15. The apparatus of claim 10, wherein the second filter is a red, long pass filter having a cutoff frequency of 630 nanometers.

16. The apparatus of claim 10, in which the means for illuminating tissue is a fiber optic light guide.

17. The apparatus of claim 16, in which the collecting means is an imaging bundle and a focusing lens disposed within the fiber optic light guide.

18. The apparatus of claim 10, wherein the first color input is a green color input and the second color input is a red color input.

* * * * *